United States Patent [19]
Jones

[11] Patent Number: 6,132,412
[45] Date of Patent: Oct. 17, 2000

[54] GENITOURINARY ELIMINATION COVERING SYSTEM

[76] Inventor: Rosemary N. Jones, 625 Bryan, Monroe County, Mo. 65275

[21] Appl. No.: 09/088,415

[22] Filed: Jun. 1, 1998

Related U.S. Application Data

[60] Provisional application No. 60/048,258, Jun. 2, 1998.

[51] Int. Cl.$^7$ ..................................................... A61F 13/15
[52] U.S. Cl. ........................... 604/400; 604/392; 604/396
[58] Field of Search .................... 602/67, 70; 604/385.1, 604/392, 400, 396

[56] References Cited

U.S. PATENT DOCUMENTS 4,795,450  1/1989  Tovar et al. .
5,547,466  8/1996  McRoberts et al. .

*Primary Examiner*—John G. Weiss
*Assistant Examiner*—Kelvin Hart

[57] ABSTRACT

This invention relates generally to a disposable type of covering or shield, which primarily is contoured and for use in conjunction with the male, and to provide a covering device for use for overlying the male anatomy, and to provide for elimination of urinary discharges, particularly amongst elderly patients, or the male who is incontinent.

8 Claims, 2 Drawing Sheets

GENITOURINARY ELIMINATION COVERING SYSTEM

This application is a non-provisional patent application based upon provisional patent application having Ser. No. 60/048,258, filed on Jun. 2, 1998, which is owned by the same inventor.

BACKGROUND OF THE INVENTION

This invention relates generally to a disposable type of shield, which primarily is contoured and for use in conjunction with the male, and to provide a covering device for use for overlying the male anatomy, and to provide for elimination of urinary discharges, particularly amongst elderly patients, or the male who is incontinent.

There are a myriad of various types of products and devices upon the market, or which have been designed, that have attempted to address the problem of male urinary incontinence. Many of these devices, though, are simply designed in conformance with the usual diaper, are relatively expensive to manufacture, impractical or too broad in their coverage to provide for comfort, and in addition, usually because of their particular contours, do not provide for the elimination or separation of the urinary discharges from the proximate skin surfaces, and as a result, cause skin irritation and infection. The usually available adult diaper simply covers the frontal peri and rectal areas of the user. Many gentlemen who utilize the adult type of diapers, because of some medical or physical impairment, do develop excoriations of the peri and rectal areas due to the caustic effects of the high levels of ammonia exposure, due to surface contact, and because of the lack of air circulation to the skin at the location of the presence of such moisture, and also because of the body heat that is contained by the full diaper, within this region. As a result, infections can, and do, frequently occur. The side effects that are recurring as a result of exposure to the caustic chemicals that are associated with this type of an impairment can be very detrimental to the patient, and lead towards other type of infections, that are just not needed at a time that the patient is required to treat the primary problem, and that is urinary incontinence.

Other prior art type of devices that have been known include the non-spattering hygienic napkin, for use by men, such as shown in the U.S. Pat. No. 4,795,450. This particular napkin only addresses the containment of the male private part, or penis, and thus further reduces the amount of air flow to the proximate skin, once again causing an increase in heat, proximal body temperature, that increases the further potential for skin break down and severe irritation upon prolonged exposure to the developed ammonia. Such an appliance, as shown in this prior art patent, when placed over the penis will also restrict movement of the gland, thus further reducing patient comfort. Furthermore, many elderly men have regressed type of male organ, that is withdrawn into their scrotum, thus making the napkin style of coverage rather useless. Such type of napkin also has a reduced capacity for retention of the discharged fluid volume.

Another invention that is available in the art is the male panty shield. This type of a device while useful for its own intended purpose, is normally impractical for most men due to their further usage of boxer shorts, or when they fail to use any type of underwear at all, particularly when subjected to this type of male malfunction. This type of a device depends upon the usage of an undergarment to hold it in place. If the undergarment is too loose in its securement, it will not make contact with the absorbent material, thus having the unresolved problem of being unable to sustain containment, and allowing for fluid migration which is equally and highly undesirable.

SUMMARY OF THE INVENTION

The current invention, though, is designed to provide for significant comfortability due to its freedom of movement for the proximate male parts, such as the penis and scrotum as contained, this device also provides for ease of its placement onto the user simply with the use of an elastic waist band, or through its securement with buttons, or hook mounts, and maintained in close proximity with the contiguous skin, leading to decreased skin exposure to the urine, a complete wicking of the urinary discharge into the absorbent portions of the designed shield, and also providing for better air flow to the organs, with further increase contact of the discharged urine with the absorbent material, and this is regardless of the anatomical size or shape of the gland, or its various positions. The pouch of this current invention will significantly assist in holding the device on, and to reduce spillage of any caustic urine, even after sustained usage.

It is, therefore, the principal object of this invention to provide a minimum sized diaper-like covering that is form fit and contoured more specifically to the male anatomy which provides for complete absorption of any discharged urine, but wicks it away from its contact with the skin, thereby reducing and preventing exposure with reduced incidence of generated infection.

The concept of this invention is to provide a genitourinary elimination maintenance system, that primarily is used in conjunction with the male patient, or with elderly men. This invention is an aid to help the male experiencing urinary incontinence.

The construction of this invention incorporates a pouch-like means, that may have an outer impervious covering layer fabricated of polymer, treated paper, or related material that prevents the migration of liquid, so as to sustain any clothing proximate or exteriorly thereof in a dry stage, and prevent wetting. The inner layer of the pouch-like member is fabricated also of a polymer or related material, as aforesaid, which is perforated, slitted, or contains means for providing migration of discharged liquid there through, to thereby allow for the shifting or movement of any liquid away from the body, thereby reducing skin exposure to caustic fluids, such as ammonia, and other byproducts of the urinary tract. Interiorly, or intermediate of the two previously described inner and outer layers is a quantity of highly absorbent material, which may be formed of any of the variety of wicking materials readily available upon the market, such as cotton, fiber, even recycled paper, or the like, and which functions as a significant wick to provide for the blotter like effects of removing the discharged urine from proximity of the body, into the interior of the pouch-like means, to store it therein, to sustain, or attempt to sustain, reasonable dryness of the proximate skin, thereby reducing the incidence of the body and the dermal to sustain infection, which may otherwise occur.

The absorbent area of the covering or shield fits over the lower abdomen, the scrotum, and the penis. Urine will flow into the device, instead of onto the pad or the proximate clothing.

The pouch of this invention incorporates a plastic bag, which is form fit, having a similar appearance to the front like adult diaper, with the penis and scrotum of the patient being located into its formed pouch, at the bottom. Since the bag is filled interiorly therein with an absorbent material, any liquid discharge immediately is absorbed through the inner polymer or related layer of material, and into the absorbent material, to draw it away from these body parts, and their exposed skin.

The pouch-like means used in the formation of this covering system, as explained, includes its various protective liners, and has the fibrous material located inside, in order to prevent contact of the skin with the wet absorbent material. The absorbent material may be either organic, synthetic, or even recycled in nature. But, the lower and back segment of the pouch is also form fitting, can be arranged upwardly into an area behind the scrotum. It will be form fitting either by elastic gathering, by having an elastic means or tape provided at the upper back edge of the pouch, to provide for its drawing together, into a enveloping or holding position, or it may include a drawstring, at that location, and which may be tightened to provide for a hold of the pouch into place, once located.

The upper edge of the pouch of the shield will include any of a variety of straps, either an elastic strap, or plastic straps that may be tied, or either of which may be held by Velcro to the upper edge of the shield, so that the strap may be adjustable in size, to form fit the dimensions of the wearer. In addition, Velcro may be used at the ends of the straps, to provide a means for tying the strap together, once tightly fitted about the patient.

As an alternative means for holding of the pouch of the shield in place, rather than a strap, the pouch may include a pair of buttonholes, and which will be spaced apart at the upper edge of the shield to those dimensions equivalent to the spacing of, for example, suspender buttons that are normally provided interiorly, at the front waist, of the pants of any wearer. Other types of buttons, snaps, adhesive holders, or the like, may also be used.

The genitourinary shield of this invention may be offered in a wide variety of range of sizes, pediatric size, extra small, small, medium, large, and the extra large, particularly where the elderly male may be involved. It can also be offered in different absorptive strengths, either scant, mild, medium, or heavy flow, depending upon the patient usage. Furthermore, it may be offered in a multitude of colors, for whatever reasons desirable, and they even be unscented, or scented, where attempts to mask odor may be required.

As previously reviewed, this invention is a diaper-like covering contoured more specifically for the male anatomy which facilitates the absorption of discharged urine. Furthermore, it provides for maintenance of the skin, and to sustain an infection free environment. Its absorbent area fits over the penis and scrotum, preventing or limiting the exposure of these male parts to discharged urine. It also promotes healthy skin due to increased air flow, as around the form fitting shield, constructed of its pouch, and allows for better air flow around its perimeter, than any diaper heretofore used in the prior art. Also, this device does not provide any covering for the posterior, which prevents absorption and migration of any urinary discharge to these areas, and which would further cause a spread of infection. As a result, when utilizing this device, undergarments may or may not be used in conjunction therewith. Contact of any discharged urine with the absorbent material will be insured, due to the wickability or absorbency of the material, and because the pouch is formed of resilient material, and because the absorbent filler material may be woven into a particular shape, or have structural integrity through the use of wire-like woven mesh, or the like, constructed therein, the moldability and sustained shape of the formed pouch will be assured.

As is well known, thousands of people, especially the older individuals, do suffer from urinary incontinence, a condition in which there is a loss of control of the urinary sphincter. Urinary stress incontinence is an even more common problem that effects people of all ages. It is the inability to prevent the escape of urine during stress, such as during laughing, coughing, sneezing, lifting or sudden movement, that causes this imperfection. It occurs frequently enough also in young women to be classified as normal, but such primarily is also a detriment primarily of the human male. Although, it is likely that a contoured shield of this current invention may also be used by the women, in order to reduce the discomfort of menstrual flow, urinary incontinence, and the like.

It is therefore, the principal object of this invention to provide a pouch formed like shield that may be suspended from the person and provide complete coverage to the male anatomy.

Another object of this invention is to provide a highly absorbent type of shield that wicks away any inadvertently discharged urine or other fluids.

Another object of this invention is to provide a pouch-like means that may be form fit with the male penis and scrotum, in order to provide not only for support, but complete removal of any discharge, and its isolation at this particular location.

Another object of this invention is to prevent migration of urinary discharges to other parts of the body, or proximate skin.

Yet another object of this invention is to provide a pouch-like shield, that contains sufficient absorbent material so that significant quantities of discharge will be suspended and sustained in isolation, until discarding.

Another object of this invention is to provide a shield-like pouch that may be suspended in a variety of ways, either by strap, straps that tie, Velcro held straps, elastic straps, or even through the use of buttons, clasps, or the like.

Another object of this invention is to provide a shield-like means that incorporates highly absorbent material that may be either formed of organic, synthetic, or even treated recycled material in their construction.

Another object of this invention is to provide a genitourinary covering that may be easily manufactured, through mass production, nested when stored or displayed, to facility its inventorying, storage, transit, and marketing.

A further object of this invention is to provide a urinary shield that may be very easy of manufacture. Still another object of this invention is to provide a shield that can be offered to different absorptive strengths, depending upon the degree of impairment experienced by the patient or wearer.

These and other objects will become more apparent to those skilled in the art upon reviewing the summary of the invention herein, and upon undertaking a study of the description of its preferred embodiment, in view of the drawings.

DESCRIPTION OF THE PREFERRED EMBODIMENT

Figure 1:
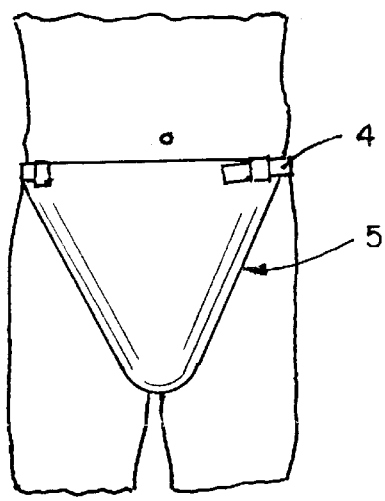
FIG. 1 is a front view of a patient wearing the genitourinary eliminating shield of this invention.
Figure 2:
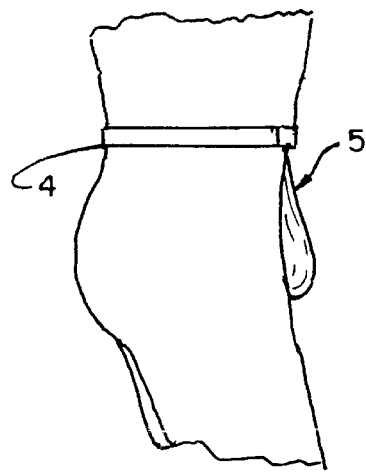
FIG. 2 is a side view thereof.

In referring to the drawings, and in particular FIGS. 1 and 2, the genitourinary elimination maintenance covering or shield S of this invention is readily disclosed. It is shown form fitting upon the male wearer.

Figure 3:
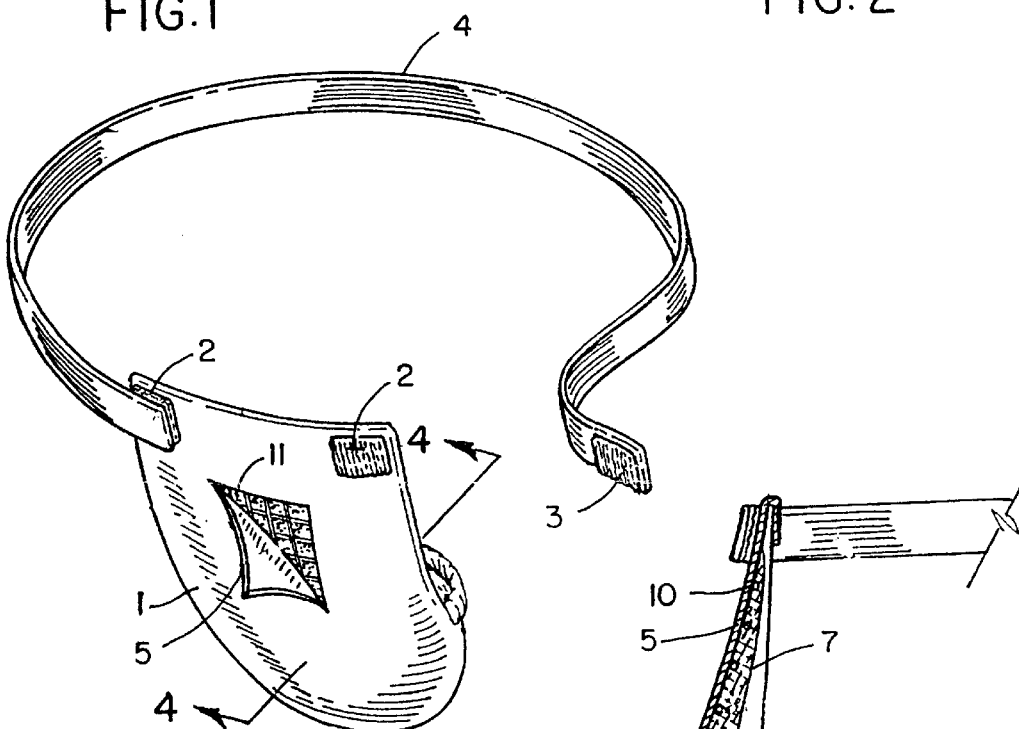
FIG. 3 is a perspective view of the shield, during its installation.
Figure 4:
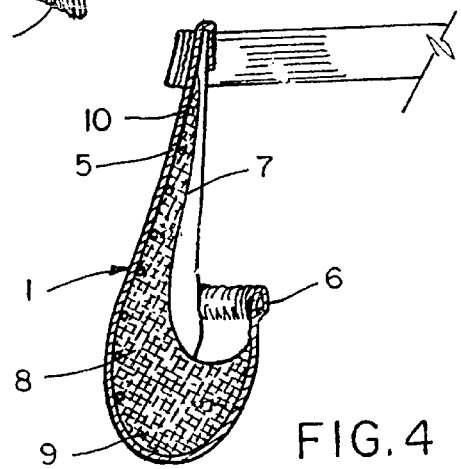
FIG. 4 is a sectional view taken along the line 4—4 of FIG. 3.

As disclosed in FIG. 3, this embodiment of the shield includes a pouch-like member 1, which at its upper end includes a series of connecting means such as the hook-and-pile fastening means 2 and 3, generally identified as Velcro, and which connects the ends of the waist band 4 tightly about the wearer, and to sustain the shield in place. As can be seen in FIG. 4, which is a cross-section of the shield, the pouch-like configuration 1 is shown. As disclosed, it includes an outer fluid impervious layer 5 which extends the full height of the pouch, and drapes around its underside, and extends up to the gathered rear portion 6 which may include an elastic band or strap therein, so as to provide for its gathering, as noted, and form fitting at the upper back edge of the emplaced scrotum. The interior of the pouch is also formed with a liner-like material, as at 7, and it also, just like the outer layer, may be fabricated of a polymer, treated paper, or other fluid impervious layer of material, but which is perforated, slitted, or the like, so as to allow for any discharged urine to flow there through, and be collected within its absorbent material 8, arranged intermediate thereof. It is just as likely, though, that the inner layer of the member may comprise just the inner surface of the absorbent material, and which readily absorbs any body fluids that discharge upon the same, during the usage and application of this invention. This absorbent material, as previously described, may be either organic, synthetic, or even formed of recycled materials, and which may be constructed of cotton, paper, fiber, or other related types of materials, so as to wick away any exposed fluids, and function as a blotter to absorb all moisture that is discharged in its vicinity, so as to draw it interiorly of the inner liner 7, and away from the male anatomy and proximate skin. As can further be noted, the absorbent material may be of a bulkier consistency at its lower region, as at 9, than at its upper region 10, because most of the fluid will drain by gravity down into the lower region, and be collected thereat, away from the vicinity of the proximate inner liner 7.

As can also be seen in FIG. 3, the absorbent material may also have woven therein, or be located intermediate the outer liner 5, and the absorbent material 8, with a woven-like form-fitting grid work or other type of structure, as at 11, in order to provide for the pouch-like formation of the shield, to maintain its shaped consistency, even during sustained usage, and even after the absorbent material becomes totally saturated with urine, during sustained usage. Such grid can be formed of plastic, wire, or related materials.

Figure 6:
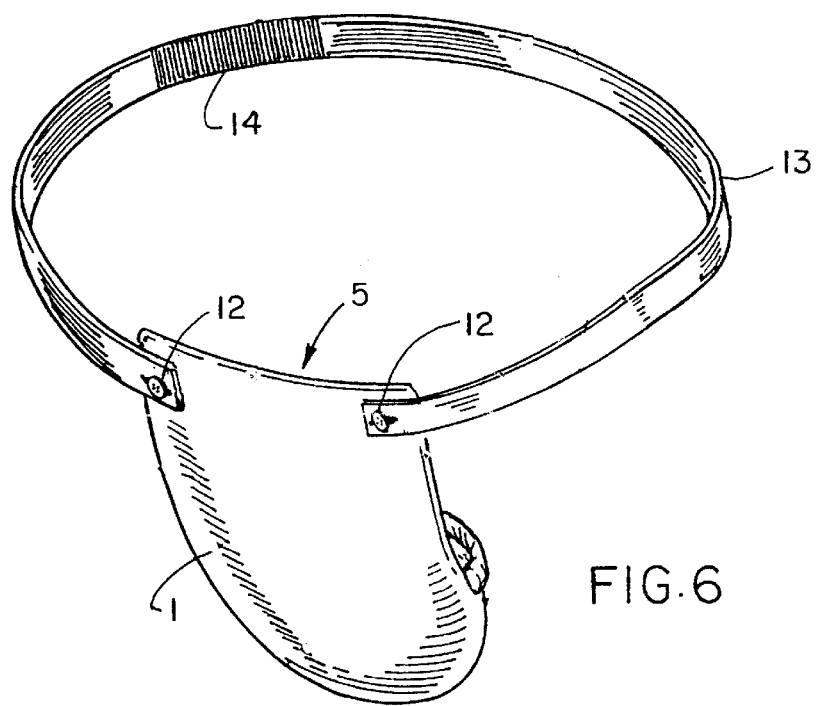
FIG. 6 discloses how an elastic type buttoned strap may be used to hold the shield in place.
Figure 7:
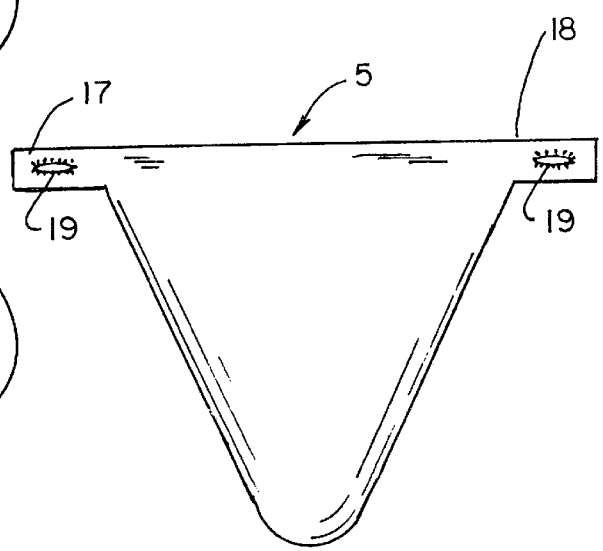
FIG. 7 discloses how buttonholes may be provided along the upper edge of the shield to provide for its connection with interior of the wearer's pants.
Figure 5:
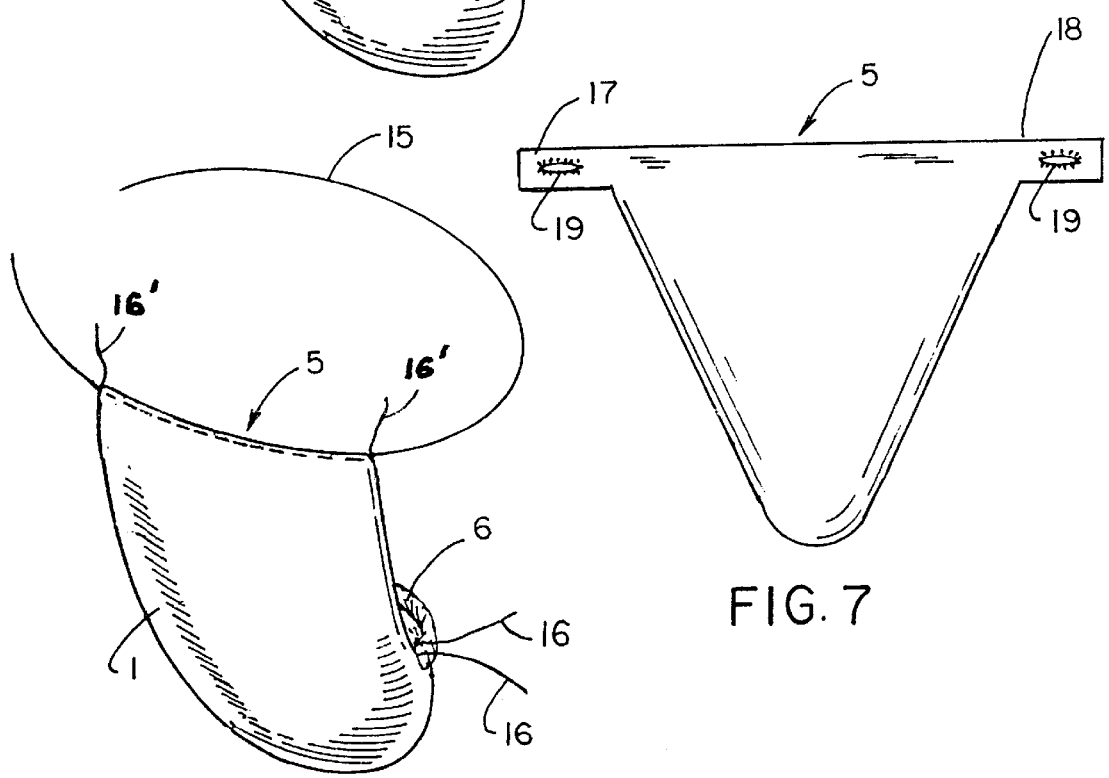
FIG. 5 indicates a modification to the shield showing how various drawstrings may be alternatively used to tighten the shield about the wearer and also the upper rear cup-like portion of the pouch to form fit the patient.

Various other configurations, or means for attachment or holding of the shield of this invention, to the body, are also disclosed in FIGS. 5 through 7. As can be noted, FIG. 6 discloses the shield S with its formed pouch 1, wherein the pouch contains buttons, clasps, or the like, as at 12, at their upper corners, and which may connect with a strap 13, of the type that may include some elastic 14 therein, so as to provide for a snug tightening of the strap about the body, and retention of the shield in place. FIG. 5 discloses the same shield, but in this particular instance, a simple string 15 secured to its upper edge, may be tightened about the body, and tied in place, as can be noted. In addition, the upper gathered section 6 at the rear portion of the formed pouch 1 may also include a draw sting 16, and which may be gathered, and tightened, in order to form fit the pouch to the male anatomy, and assure its retention in place, for reasons as previously described. Or, a drawstring $16^1$, one on either side, can be used to gather the pouch about the various body parts desired to be covered. Other elastic like means may be located within the section 6 to provide for a gathering thereat. In addition, such draw string may also be arranged vertically, in conjunction with the upper gathered section 6 of the formed pouch, with said draw strings extending upwardly, into proximity with the upper edge of the fluid impervious layer 5, so as to facilitate the draw of the strings, and their tightening in formation of the pouch, and its upper gathered section 6, when applied during usage.

FIG. 7 discloses the shield S of this invention, and where its upper segment may have integrally form tabs 17 and 18, and which may include buttonholes formed therein, as at 19, and which may be spaced apart an approximate dimension that is equivalent to the location of buttons normally formed and applied interiorly of men's trousers, and to which suspenders may be attached, but in this particular instance, the shield S of this invention may be applied thereto, and its lower back portion 6 gathered, and tightened, so as to retain the pouch in position with respect to the male anatomy, and function for its intended purposes.

It is also conceivable that the means for holding the upper segment of the shield of this invention, in place, and to the body, in lieu of the usage of Velcro 2 and 3, may be an adhesive or other type of sticky tape connector, that may be applied between the ends of the waistband 4, and the front surface, at least at one side, of the pouch-like member 1, as can be understood.

As is known in the art, the absorbent material that may be located within the absorbent pouch area of this covering system, may be that which is readily used in the art, such as a wood pulp fluff, and in certain instances, in order to even further enhance the absorbency of such material, it may be treated with a composition similar to poly sodium acrylate, to further enhance the absorbency of the system of this invention. In addition, the inner layer of material, which overlies the absorbent material, may contain sufficient means to allow for migration of any fluids interiorly thereof, such as, as previously explained, through the use of perforations, slits, apertures, or the like, in order to render more effective the absorbent material of this system.

Variations or modifications to the subject matter of this invention may occur to those skilled in the art upon reviewing the summary of the invention as provided herein. Such variations or modifications, if within the scope of this invention, are intended to be encompassed within the subject matter of this disclosure, and covered by the claims herein. The description of the preferred embodiment as provided herein is done so for illustrative purposes only.

What is claimed is:

1. A genitourinary cover for a male person, the cover comprising a front portion having a top and a bottom, an integral pouch portion at a bottom of the front portion; and a support positioned near the top of the cover front portion to maintain the cover in place when being worn; the pouch being sized and shaped to contain the penis and scrotum of a male and including a front, a bottom, and a back; the pouch front being continuous with the cover front portion; the pouch back having an upper edge spaced below the upper edge of the front portion when worn; the cover further including an outer layer made of a fluid impervious material, an inner layer, and an absorbent material disposed between the inner and outer layers; the inner layer is made of a fluid impervious material, the inner layer having openings therein to allow for urine to be absorbed by the absorbent material; an elastic band in the periphery of the pouch portion, the elastic band being positioned on the pouch to substantially maintain the shape of the pouch; the absorbent material has a depth between the inner and outer layers, the depth of the absorbent material in the pouch portion of the covering being greater than the depth of the absorbent material in the upper front portion of the cover, the cover including left and right side edges, the support including a band which extends from the left edge to the right edge, the band being sized to extend around the waist of a wearer.

2. The genitourinary cover of claim 1 including a grid structure between the inner and outer layers of the cover; the grid structure being made of a material which will substantially maintain the absorbent material in place in the cover when worn.

3. The genitourinary cover of claim 1 wherein the band is a draw string, the draw string having a first portion which extends from the cover left edge and a second portion which extends from the cover right edge.

4. The genitourinary cover of claim 1 and including a draw string cooperating with the upper edge of the pouch, and provided for drawing and raising the pouch upwardly, into position for support and holding the identified male body parts.

5. The genitourinary cover of claim 1 wherein the band comprises a strip of material which is releasably securable to at least one edge of cover.

6. The genitourinary cover of claim 5 wherein a hook and pile fastener is used to secure the band to at lest one edge of the cover; the hook and pile fastener including a hook section on one of the band and the cover front edge and a pile section on the other of the band and cover front edge.

7. The genitourinary cover of claim 5 wherein a button is used to secure the band to at least one edge of the cover.

8. The genitourinary cover of claim 5 wherein the band is elastic.

* * * * *